United States Patent
Blanchard et al.

(10) Patent No.: US 6,441,165 B2
(45) Date of Patent: Aug. 27, 2002

(54) PROCESS FOR THE PREPARATION OF 11-AMINO-3-CHLORO-6, 11-DIHYDRO-5, 5-DIOXO-6-METHYL-DIBENZO[C,F][1,2] THIAZEPINE AND APPLICATION TO THE SYNTHESIS OF TIANEPTINE

(75) Inventors: Jacky Blanchard, Ste-Marie-des-Champs; Hugues Turbe, Villers-Ecalles; Daniel Brigot, Ste-Marie-des-Champs, all of (FR)

(73) Assignee: Les Laboratoires Servier, Courbevoie (FR)

(*) Notice: Subject to any disclaimer, the term of this patent is extended or adjusted under 35 U.S.C. 154(b) by 0 days.

(21) Appl. No.: 09/821,221

(22) Filed: Mar. 29, 2001

(30) Foreign Application Priority Data

Mar. 31, 2000 (FR) .............................. 00 04111

(51) Int. Cl.[7] ........................................... C07D 281/02
(52) U.S. Cl. ..................................................... 540/549
(58) Field of Search .......................................... 540/549

(56) References Cited

FOREIGN PATENT DOCUMENTS

| EP | 671 173 | * | 9/1995 |
| FR | 1566191 | | 5/1969 |
| FR | 2104728 | | 4/1972 |

OTHER PUBLICATIONS

Caplus printout for Labrid et al., Structure–Activity Relationships of Tricyclic Antidepressants, With Special Reference to Tianeptine, Clin. Neuropharmacol., vol. 11, Suppl. 2, pp. S21–S31, 1988.*

* cited by examiner

Primary Examiner—Brenda Coleman
(74) Attorney, Agent, or Firm—The Firm of Hueschen and Sage; G. Patrick Sage

(57) ABSTRACT

Process for the industrial synthesis of the compound of formula (I):

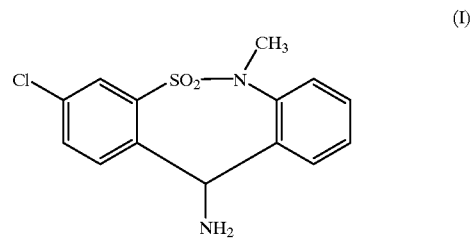

and its addition salts.

Application to the synthesis of tianeptine and its pharmaceutically acceptable salts.

2 Claims, No Drawings

PROCESS FOR THE PREPARATION OF 11-AMINO-3-CHLORO-6, 11-DIHYDRO-5, 5-DIOXO-6-METHYL-DIBENZO[C,F][1,2] THIAZEPINE AND APPLICATION TO THE SYNTHESIS OF TIANEPTINE

The present invention relates to a new process for the industrial synthesis of 11-amino-3-chloro-6,11-dihydro-5,5-dioxo-6-methyl-dibenzo[c,f][1,2]thiazepine of formula (I):

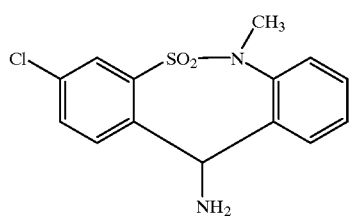

(I)

and its addition salts.

BACKGROUND OF THE INVENTION

The compound of formula (I) is an important intermediate in the synthesis of tianeptine of formula (II):

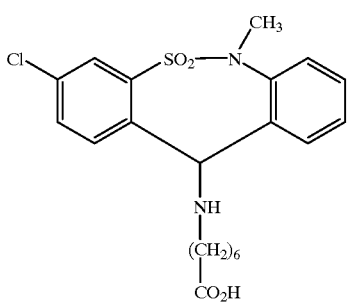

(II)

and its pharmaceutically acceptable salts.

The compound of formula (II) and its addition salts have valuable pharmacological properties. They are stimulants of serotonin uptake, which makes them useful in the treatment of depression and anxiety.

The compound of formula (II), its preparation and its use in therapeutics have been described in Patent Specification FR 2 104 728.

In view of its pharmaceutical value, it was important to be able to produce the compound in an optimum yield and purity, using available, unproblematic starting materials and using a synthesis process that could be readily converted to the industrial scale.

DESCRIPTION OF THE PRIOR ART

Patent Specification FR 2 104 728 describes the preparation of the compound of formula (II) by reacting 3,11-dichloro-6,11-dihydro-5,5-dioxo-6-methyl-dibenzo[c,f][1,2]-thiazepine with ethyl 7-amino-heptanoate.

That process does not, however, enable the compound of formula (II) to be obtained in a satisfactory yield and purity, in particular because of the instability of the ethyl 7-amino-heptanoate in the reaction mixture.

Patent Specification EP 0 671 173 describes the preparation of an isomer of the compound of formula (II) by reacting the amine of formula (I) with ethyl 7-bromo-heptanoate. That process is very valuable as it provides tianeptine of formula (II) in a much better yield and purity. Access to the starting amine of formula (I) is not described, however.

In the absence of a process for the synthesis of that intermediate, detailed research has been carried out, resulting in the development of an especially valuable industrial synthesis process enabling the compound of formula (I) to be obtained in an excellent yield and purity in 2 steps using unproblematic starting materials.

DETAILED DESCRIPTION OF THE INVENTION

More specifically, the invention relates to a process for the preparation of the compound of formula (I), which process is characterised in that the ketone of formula (III):

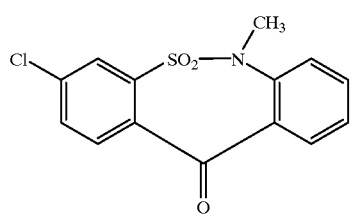

(III)

is reacted with sodium borohydride, in a two-phase medium (chlorinated solvent such as, for example, chloroform, dichloromethane or dichloroethane/aqueous sodium hydroxide solution), in the presence of N-dodecyl-N-methyl-diethanolammonium bromide, to yield the alcohol of formula (IV):

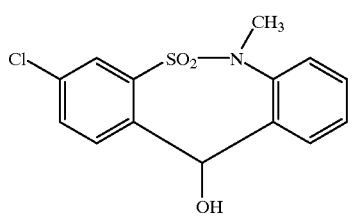

(IV)

which, as a suspension in a chlorinated solvent such as, for example, chloroform or dichloromethane, is treated with gaseous hydrogen chloride to yield the chloride of formula (V):

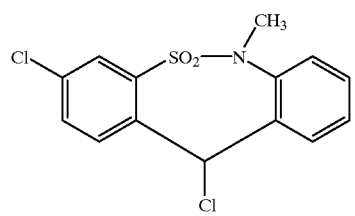

(V)

which is then, without being isolated, treated with gaseous ammonia, while maintaining the temperature between 25 and 35° C., to yield the compound of formula (I), which is, if desired, converted into an addition salt such as the hydrochloride.

This process is especially valuable for the following reasons:

Reduction of the ketone of formula (III) by sodium borohydride in a methanolic medium is known and has been described, in particular, in Patent Specification FR 1 566 191. On an industrial scale, however, the treatment of such reaction mixtures is laborious, in particular requiring the evaporation of large amounts of methanol. The Applicant has found that it is especially advantageous to carry out the said reduction in a chlorinated solvent such as, for example, dichloroethane, dichloromethane or chloroform, because the alcohol formed can then be isolated directly by means of filtration.

When carried out in a non-hydroxylated solvent, the reduction of ketones by sodium borohydride requires the use of a phase-transfer catalyst. The Applicant has found that the use of N-dodecyl-N-methyl-diethanolammonium bromide in an amount corresponding to from 1 to 3% by weight of the ketone used allows complete and very rapid (2–3 hours) reduction of the ketone of formula (III). By way of comparison, the use of tetrabutylammonium hydrogen sulfate, a customary phase-transfer catalyst, requires a reaction time that is twice as long.

The resulting alcohol of formula (IV) is converted into the chlorinated compound of formula (V) by the action of gaseous hydrogen chloride, and then, after degassing, the chlorinated compound is treated with ammonia in situ to yield the primary amine of formula (I).

This procedure has the advantage of avoiding isolation of the intermediate chlorinated compound, thereby limiting the number of operations.

The preparation of primary amines by reacting halogenated compounds with ammonia generally yields rather unsatisfactory results: the yields are low and large proportions of secondary products (secondary and tertiary amines) are formed. The Applicant has found operating conditions that, surprisingly, allow the primary amine of formula (I) to be obtained in good yields starting from the corresponding chloride of formula (V). These conditions consist of passing a stream of ammonia through a suspension of the chloride of formula (V) in a chlorinated solvent such as chloroform or methylene chloride while maintaining the temperature of the reaction medium at about 30° C. The product is then advantageously isolated from the reaction medium in the form of the hydrochloride. Under those conditions, the yield, starting from the alcohol of formula IV, is more than 75% and the product obtained contains less then 0.3% of the secondary amine of formula (VI):

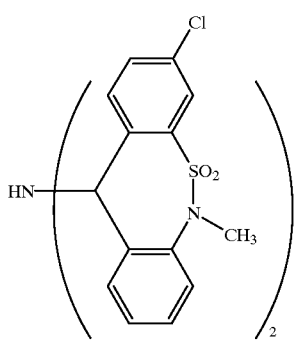

(VI)

The resulting hydrochloride has very good purity, making its use in the synthesis of tianeptine of formula (II) especially advantageous.

By way of illustration, reacting the 11-amino-3-chloro-6,11-dihydro-5,5-dioxo-6-methyl-dibenzo[c,f][1,2]thiazepine hydrochloride obtained according to the invention with ethyl 7-bromoheptanoate in an ethanolic medium under reflux, in the presence of sodium hydrogen carbonate, allows tianeptine of formula (II) to be obtained in a highly satisfactory yield and purity.

The latter compound is then converted, if desired, into its sodium salt by the addition of sodium hydroxide. The resulting sodium salt of tianeptine has excellent purity and contains less than 0.4% impurities (measured by liquid chromatography on a C18 column).

In particular, it contains less than 0.1% of the disubstitution product of formula (VII):

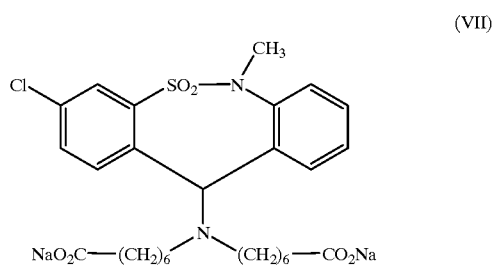

(VII)

and does not contain the impurity of formula (VI).

The following Examples illustrate the invention and do not limit it in any way.

EXAMPLE 1

3-Chloro-6,11-dihydro-5,5-dioxo-11-hydroxy-6-methyl-dibenzo -[cf][1,2]thiazepine 100 kg of 3-chloro-6,11-dihydro-6-methyl-5,5,11-trioxo-dibenzo[c,f][1,2]thiazepine, 1.8 kg of N-dodecyl-N-methyl-diethanolammonium bromide and 100 liters of chloroform are introduced into a stirred reactor. The mixture is then heated to reflux and then a solution of 4.6 kg of sodium borohydride in 140 liters of water and 0.7 kg of 30% sodium hydroxide solution is added. After the evolution of gas has ceased, the reaction mixture is brought to ambient temperature and the precipitate obtained is filtered off, washed with water and dried. The title compound is thereby obtained in a yield of 97%. Melting point: 199–200° C.

EXAMPLE 2

11-amino-3-chloro-6,11-dihydro-5,5-dioxo-6-methyl-dibenzo -[c,f][1,2]thiazepine hydrochloride A suspension of the alcohol described in Example 1 (100 kg) in chloroform is treated at 5° C. with a stream of gaseous hydrogen chloride and then, after removing the excess of hydrogen chloride by degassing with nitrogen, the suspension of chloride obtained is treated with a stream of gaseous ammonia, while maintaining the temperature of the reaction medium at 30° C. The excess of ammonia is then removed with a stream of nitrogen; water is then added, the mixture is separated and the organic phase is washed with water and then treated with 30 kg of concentrated hydrochloric acid. The precipitate obtained is collected by filtration, washed with chloroform and then dried. The title compound is thereby obtained in a yield of 79%. Melting point: 193–197° C.

We claim:

1. A process for the industrial synthesis of 11-amino-3-chloro-6,11-dihydro-5,5dioxo- 6-methyl-dibenzo[c,f][1,2]thiazepine of Formula (I):

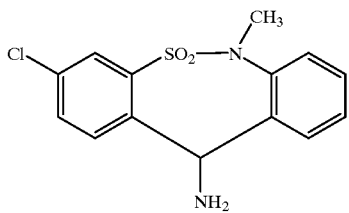
(I)

and its addition salts, wherein the ketone of Formula (III):

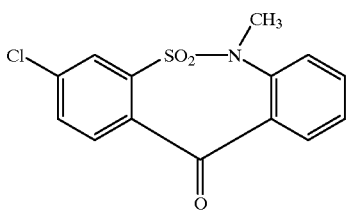
(III)

is reacted with sodium borohydride, in a two-phase medium (chlorinated solvent selected from chloroform, dichloromethane/aqueous sodium hydroxide solution), in the presence of N-dodecyl-N-methyl-diethanolammonium bromide, to yield the alcohol of Formula (IV):

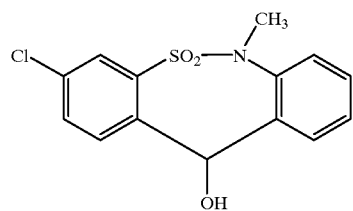
(IV)

which, as a suspension in a chlorinated solvent selected from chloroform or dichloromethane, is treated with gaseous hydrogen chloride to yield the chloride of Formula (V):

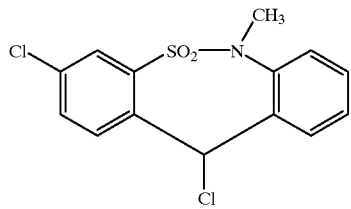
(V)

which is then, without being isolated, treated with gaseous ammonia, while maintaining the temperature between 25 and 35° C., to yield the compound of Formula (I), which is, if desired, converted into an addition salt.

2. A process of claim 1, wherein the level of the secondary amine of Formula (VI)

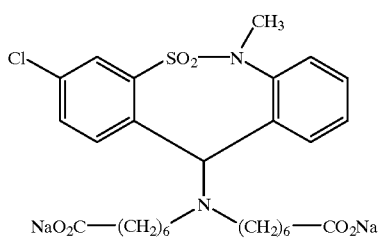
(VII)

in the hydrochloride of the compound of Formula (i) formed is less than 0.3%.

* * * * *

UNITED STATES PATENT AND TRADEMARK OFFICE
CERTIFICATE OF CORRECTION

PATENT NO. : 6,441,165 B2
DATED : August 27, 2002
INVENTOR(S) : Jacky Blanchard et al.

It is certified that error appears in the above-identified patent and that said Letters Patent is hereby corrected as shown below:

<u>Title page,</u>
Item [73], Assignee, "Les Laboratories Servier" should be -- Les Laboratoires Servier --.

<u>Column 6,</u>
Claim 2, Formula VI: " (VII) "

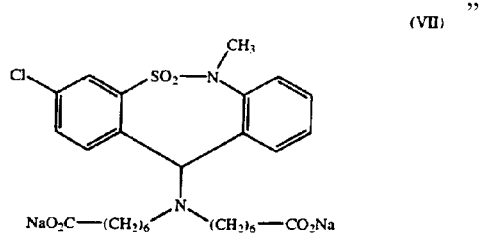

should be --

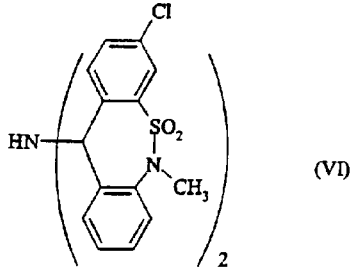

(VI)

--

Signed and Sealed this

Seventh Day of January, 2003

JAMES E. ROGAN
*Director of the United States Patent and Trademark Office*